(12) United States Patent
Rogers et al.

(10) Patent No.: US 10,271,993 B2
(45) Date of Patent: Apr. 30, 2019

(54) NANO-OTOLOGIC PROTECTIVE EQUIPMENT FOR IMPACT NOISE TOXICITY AND/OR BLAST OVERPRESSURE EXPOSURE

(75) Inventors: Rick Rogers, Needham, MA (US); Brendan Clifford, Encinitas, CA (US); Robert M. Westervelt, Lexington, MA (US); John W. Hutchinson, Cambridge, MA (US); Howard A. Stone, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1419 days.

(21) Appl. No.: 12/160,558

(22) PCT Filed: Jan. 10, 2007

(86) PCT No.: PCT/US2007/060346
§ 371 (c)(1),
(2), (4) Date: Feb. 11, 2009

(87) PCT Pub. No.: WO2007/082241
PCT Pub. Date: Jul. 19, 2007

(65) Prior Publication Data
US 2011/0197899 A1    Aug. 18, 2011

Related U.S. Application Data

(60) Provisional application No. 60/757,673, filed on Jan. 10, 2006, provisional application No. 60/747,246, filed on May 15, 2006.

(51) Int. Cl.
*A61N 1/36* (2006.01)
*A61F 11/08* (2006.01)

(52) U.S. Cl.
CPC .......... *A61F 11/08* (2013.01); *A61N 1/36036* (2017.08)

(58) Field of Classification Search
USPC ......... 128/864–865, 967, 866; 181/130, 132, 181/137
See application file for complete search history.

(56) References Cited

U.S. PATENT DOCUMENTS

| | | |
|---|---|---|
| 1,148,849 A | 8/1915 | Mallock |
| 2,487,038 A | 11/1949 | Baum |

(Continued)

FOREIGN PATENT DOCUMENTS

| | | |
|---|---|---|
| DE | 2319732 A1 | 10/1974 |
| WO | 0176520 A1 | 10/2001 |

OTHER PUBLICATIONS

"Structures of the human ear"; image provided by Encyclopedia Britannica; accessed from www.britannica.com.*

(Continued)

*Primary Examiner* — Ophelia A Hawthorne
*Assistant Examiner* — Caitlin A Carreiro
(74) *Attorney, Agent, or Firm* — Michael T. Abramson; Holland & Knight LLP

(57) ABSTRACT

An apparatus preventing hearing loss having a body made of soft compliant material having first and second ends and a channel extending therethrough, an acoustically limp material adjacent one end of the body with the acoustically limp material having a hole therein aligned with the channel extending through the body, component film, or other structure covering or sealing the opening in the acoustically limp material. The film may be a high-strength polymer less than 10 micrometers thick. A plurality of channels may extend through the body and a plurality of corresponding holes may be provided in the acoustically limp material. The film (Continued)

covers or seals the holes in the acoustically limp material. The film may behave like a flap to close in response to high energy sound waves. The flap shuts from the high intensity shock wave. The body may have shape to fit in an ear canal.

16 Claims, 11 Drawing Sheets

(56) References Cited

U.S. PATENT DOCUMENTS

| | | | |
|---|---|---|---|
| 3,730,181 A * | 5/1973 | Fling | A61F 11/08 |
| | | | 128/868 |
| 3,842,829 A | 10/1974 | Ellis | |
| 4,055,233 A * | 10/1977 | Huntress | 181/135 |
| 4,349,082 A | 9/1982 | Gastmeier | |
| 4,540,063 A | 9/1985 | Ochi et al. | |
| 4,807,612 A | 2/1989 | Carlson | |
| 4,852,683 A | 8/1989 | Killion | |
| 5,113,967 A | 5/1992 | Killion et al. | |
| 5,553,096 A | 9/1996 | Messman | |
| 5,554,096 A | 9/1996 | Ball | |
| 6,068,079 A * | 5/2000 | Hamery | A61F 11/08 |
| | | | 128/864 |
| 6,070,693 A | 6/2000 | Hamery | |
| 6,148,821 A | 11/2000 | Falco | |
| 6,164,409 A * | 12/2000 | Berger | 181/135 |
| 6,241,042 B1 | 6/2001 | Falco | |
| 6,830,124 B2 * | 12/2004 | Chiang | 181/135 |
| 7,185,655 B1 * | 3/2007 | Redon | 128/864 |
| 7,313,245 B1 * | 12/2007 | Shennib | 381/325 |
| 7,477,753 B2 | 1/2009 | Buckley et al. | |
| 2001/0007050 A1 | 7/2001 | Adelman | |
| 2003/0037989 A1 | 2/2003 | Widmer et al. | |
| 2003/0159878 A1 | 8/2003 | Hakansson et al. | |
| 2004/0069310 A1 * | 4/2004 | Falco | A61F 11/08 |
| | | | 128/864 |
| 2004/0136555 A1 | 7/2004 | Enzmann | |
| 2005/0033383 A1 | 2/2005 | Ibrahim et al. | |
| 2005/0094835 A1 * | 5/2005 | Doty | A61F 11/08 |
| | | | 381/328 |
| 2005/0238506 A1 | 10/2005 | Mescher et al. | |
| 2005/0274568 A1 | 12/2005 | Falco et al. | |
| 2006/0042867 A1 | 3/2006 | Haussmann et al. | |
| 2006/0213525 A1 | 9/2006 | Matsumoto | |
| 2007/0102006 A1 | 5/2007 | Falco | |
| 2007/0102007 A1 | 5/2007 | Falco | |
| 2007/0125590 A1 | 6/2007 | Oberdanner | |
| 2007/0183606 A1 | 8/2007 | Doty | |
| 2007/0249959 A1 | 10/2007 | Kiefer et al. | |
| 2012/0033823 A1 | 2/2012 | Rogers et al. | |

OTHER PUBLICATIONS

"NatoHandbook.pdf"; Nato Handbook on the Medical Aspects of NBC Defensive Operations (Army Field Manual FM 8-9 Part I/Chptr 3; Feb. 1, 1996) (accessed Mar. 5, 2015 from https://web.archive.org—dated Nov. 9, 1999).*

"Film_merriamwebsterdefinition.pdf"; Definition of "film"; www.merriam-webster.com (accessed Mar. 5, 2015).*

Supplementary European Search Report and European Search Opinion dated Nov. 21, 2011 (8 pgs.).

International Search Report with Written Opinion, dated Feb. 14, 2008, received in international patent application No. PCT/US 07/60346, 3 pgs.

* cited by examiner

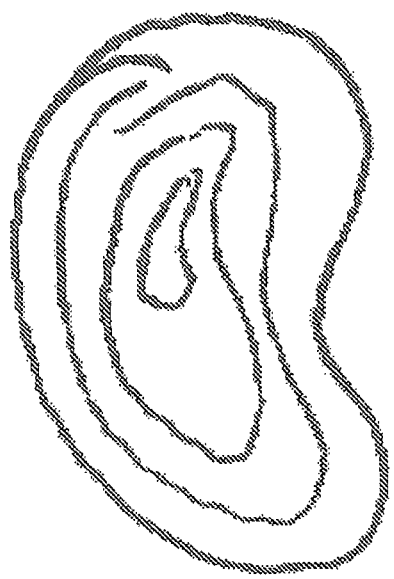
FIG. 6(b)　　　　　FIG. 6(a)
FIG. 7(b)　　　　　FIG. 7(a)

NANO-OTOLOGIC PROTECTIVE EQUIPMENT FOR IMPACT NOISE TOXICITY AND/OR BLAST OVERPRESSURE EXPOSURE

RELATED APPLICATION

The subject application is a U.S. National Stage application that claims the priority of International Application No. PCT/US07/60346, files on 10 Jan. 2007, which claims the benefit of U.S. Provisional Application No. 60/757.673, filed on 10 Jan. 2006 and U.S. Provisional Application No. 60/747,246, files on 15 May 2006.

The aforementioned prior application is hereby incorporated by reference in its entirety.

STATEMENT REGARDING FEDERALLY SPONSORED RESEARCH OR DEVELOPMENT

Not Applicable.

BACKGROUND OF THE INVENTION

Field of the Invention

The present invention relates to the field of prevention of post-concussive hearing trauma, and more specifically to physical devices, designed to be worn in the ear canal or affixed to the outer ear to block extreme shock wave damage to the hearing organ.

Brief Description of the Related Art

There is a need for devices that provide protection from blast overpressure as experienced by military personnel on a battlefield. Communication is the single most important asset of our battlefield forces. Combat elements function as a team and must be able to immediately react to unanticipated operational contingencies. Instantaneous and uninterrupted communication is fundamentally important and great effort has been made to insure efficient and redundant communication within and among tactical units in the field. However, a crucial aspect of this communication network has been overlooked—blast induced hearing loss. Frontline troops injured by explosions currently experience 64% hearing loss, and represent an instantaneous reduction in the immediate effective in-theater force, affecting the most critical element in the entire chain—the advance-line soldier.

For over 500 years, national entities have used explosive charges to wage war. Front line medical assets; improvements in surgical techniques and the creation of Shock Surgical Trauma Teams have significantly reduced the mortality radius from explosive impacts. Use of individual protective gear and body armor mitigate dismemberment and secondary limb damage in range of explosives allowing prolonged duration of the effective force on the battlefield. Hearing damage encountered in what we term the otologic disablement zone extending hundreds of meters away from the impact area remains an unaddressed component of battlefield morbidity and tactical incapacitation.

In regional proximity to the target, an explosive charge can produce a high-pressure shock wave with specific physical pressures which not only rupture the eardrum, displacing the middle ear ossicles, but also destroy inner ear sensory cells in the specific frequency ranges most utilized for interpersonnel communication. This acute hearing loss results from sharp impulse rise in sound wave intensity produced by proximity to battlefield explosions. The damage is immediate and irreversible. Soldiers within the otologic disablement zone often do not exhibit any outward sign of hearing impairment just after exposure other than being unable to respond to commands. Battlefield management of the effective force assets become secondarily compromised when the disabled team members are unable to respond to commands. This loss of unit cohesion impedes the attainment of mission objectives. Valuable time is lost as the effective force adapts to this compromised situation.

According to the office of the Army Surgeon General, hearing loss in soldiers sustained to blast injuries are running 64%, by far the highest category of battlefield injuries, resulting in significant reduction in effective force in the current War Against Terrorism. The year 2004 had the highest rate of increase in combat injuries hearing loss since records began to be kept in the mid $20^{th}$ century, a period that included for example; WWII, the Korean War, The Vietnam Conflict, the Marine deployment in Lebanon, The Gulf War, and OIF/OEF.

In the 2005 survey of hearing protector efficacy, under operational conditions, it was found that all the tested devices attenuated C-weighted peak level to less than 130 dB, well below the sound peaks experienced in explosions encountered in OIF. In practice, these devices attenuated noise by only 10-30 dB.

Proximity to explosion is more important that size. Studies on conventional bomb blasts ranging from 1 to 20 kg of TNT confirmed that proximity to explosion is more important to the size of the charge. At distances greater than 6 meters victims will probably not have mortal wounds. A SCUD missile explosion in military personnel housing injured the ears of 172 individuals. Of the 86 hospitalized, 76% had ear drum perforations. Distances to explosion were measured and used to construct mathematical model of estimated wave form. Fifty percent of soldiers will sustain a ear drum perforation at 185 dB (15 PSI).

Middle ear damage, such as Tympanic membrane perforation is always an indication of cochlear damage. An important point requires consideration. Tympanic membranes can be surgically repaired. However, there are no medical/surgical procedures to repair cochlear damage.

As in military applications, protection to the hearing organ is important in occupational and industrial settings. Impact noise in the industrial sector presents a problem similar to blast overpressure in the military sector. According to the U.S. Department of Labor, 28.4 per 10,000 workers will have recordable hearing loss (2004) US Dept Labor. Ten million have experienced permanent hearing loss, 30 million are exposed to dangerous noise levels daily (NIOSH)

Industrial Devices such as electronic ear muffs amplify outside noise so those with impaired hearing can hear warning bells. The problem is that they transmit noise and directed communication with equal intensity making no distinction between the two. Although they do not electronically transmit noise over a set dB range (often set to >85 dB), they are unable to intercept harmful sound energy which continue onto the middle and inner ear unabated.

A decibel is a sound pressure level. A whisper is 20-30 dB, normal speech is approximately 50-60 dB. A jet engine at 30 meters is 150 dB. A loud factory is 90 dB. A pneumatic hammer at 2 meters is 100 dB. The Krakatoa explosion at 100 miles was 180 dB. A rifle being fired is 140 dB. OSHA defines dangerous hearing loss at greater than 85 dB over a normal 40 hour work week. The standards in other parts of the world are more stringent.

The Israeli medical association reported that 33 out of 34 of people who survived a suicide terrorist attack on a municipal bus sustained hearing damage, yet all patients had normal electronystagmography indicating vestibular function remained unaffected even in close proximity to the blast. i.e. the bony encasement of the semicircular canals protected them against the blast overpressure force while the more vulnerable hearing organs were uniformly damaged.

In past, various attempts have been made to provide earplug or ear protectors. Such past attempts include U.S. Pat. No. 4,807,612 entitled "Passive Ear Protector," U.S. Pat. No. 4,852,683 to "Earplug with Improved Audibility," U.S. Pat. No. 5,113,967 entitled "Audibility Earplug," U.S. Pat. No. 6,070,693 entitled "Hearing Protector Against Loud Noise," and U.S. Pat. No. 6,148,821 entitled "Selective Nonlinear Attenuating Earplug." While these past attempts may have provided some attenuation of or protection against loud noises, they did not provide the protection provided by the present invention in combination with not substantially limiting or adversely affecting normal hearing.

SUMMARY OF THE INVENTION

The present invention prevents hearing damage from occurring by means of highly engineered ear protection utilizing microdevices and components, inserted into the ear canal of individuals or worn as a covering over the outer ear prior to military or industrial operations. The solutions are based on multidisciplinary problem-based learning approach to understand the at-risk anatomical features of the hearing organ, a thorough understanding of hearing physiology, firsthand medical assessment of soldiers injured in battle, and engineering application of the most up-to-date nanotechnology principles and designs. The devices resulting from the present invention hold no resemblance to hearing aids, which only filter or amplify selected sounds. Instead, the devices in accordance with the present invention intercepts high energy acoustic waves and/or reflect acoustic energy away from the ear canal, and is transparent to low intensity sound waves for normal hearing and ambient environments.

In a preferred embodiment, the present invention is an apparatus for preventing hearing loss. The apparatus comprises a body made of a soft compliant material having first and second ends and a channel or sound-transmitting polymer tube extending therethrough, an acoustically limp material adjacent one of the ends of the body with the acoustically limp material having a hole therein aligned with the channel extending through the body, and component, a film, disc or other structure covering or sealing the opening in the acoustically limp material. The film or disc may be formed of a high-strength polymer material and may be one or more micrometers in thickness. Rather than having a single channel extending through the body, a plurality of channels may extend therethrough and a plurality of corresponding holes may be provided in the acoustically limp material. The diameter of each hole or channel may be 1 millimeter, or less. The film, disc or other structure covers or seals the plurality of holes in the acoustically limp material. The body may cylindrical in shape or may have another shape to fit snugly in a human ear canal.

In another disclosed embodiment, an apparatus for preventing hearing loss according to the present invention comprises a power supply, an energy activated sensor, an input device for receiving sound, an output device for transmitting signals toward an eardrum, a vacuum tube chamber substantially between the input device and the output device, and a membrane surrounding at least the input device, the vacuum tube chamber and the output device. The input device, the output device, the vacuum tube chamber and the membrane may form at least part of an assembly that fits within a person's ear canal. The energy activated sensor may comprise a housing and a plurality of diodes. Alternatively, the energy activated sensor may comprise a flexible membrane, a mirrored element connected to the flexible membrane, an LED, a first diode detector array, a second diode detector array, and a switch; wherein the LED transmits light toward the first diode detector array. During a normal operation the first diode detector array receives light from the LED, thereby causing the switch to be in a first state. During reception of an acoustic shock wave, the mirrored element is displaced to a position in which is deflects light from the LED away from the first diode detector array and toward the second diode array, thereby causing the switch to be in a second state.

In a still another embodiment of the invention, an apparatus for preventing hearing loss comprises an assembly comprising first and second reflecting discs, an elastic nanoparticle balloon between the first and second reflecting discs, the balloon comprising a membrane filled with nanoparticles and a low viscosity fluid, wherein the nanoparticles form a disc-like structure when said balloon is compressed, a membrane surrounding the assembly, an energy activated sensor, and an energy source for supplying energy to said assembly and said sensor.

In a still another preferred embodiment of the invention, an apparatus for preventing hearing loss comprises a housing having first and second ends, a length of the housing extending between the first and second ends, a first plurality of empty microtubes substantially parallel to the length of the housing, a second plurality of microtubes substantially parallel to the length of said housing, wherein each of the second plurality of microtubes is substantially filled with a stack of discs, wherein each disc comprises a body, at least one sound aperture, an alignment pad and a disalignment pad, a first winding around each of said second plurality of microtubes for causing alignment of the apertures in the stack of discs in the microtube; and a second winding around each of the second plurality of microtubes for causing disalignment of the sound apertures in the stack of discs in the microtube.

In a still another embodiment of the present invention, an apparatus for preventing hearing loss comprises a housing, a power supply, a field coil, an energy-activated switch, and an antenna. The switch activates the field coil to generate an electromagnetic field that is directed by the antenna toward a cochlea of an ear when an acoustic shock wave is received at the switch to substantially paralyze outer hair cells on the cochlea during the acoustic shock wave.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which:

FIGS. 6(a) and (b) are top and side views illustrating the structure of a compressed silicon membrane filled with nanoparticles forming a portion of the fourth embodiment of the invention.

DETAILED DESCRIPTION OF THE PREFERRED EMBODIMENTS

The ear canal is the most vulnerable point of entry into the hearing organ for damaging sound waves. The human body has already supplied evidence for the protective nature of bone. The only organ fully encased in bone is the vestibular system, known to contain the body's balance and position receptors. Even though the semicircular canals are only millimeters away from the hearing organ and have delicate sensory cells similar to the loss of cochlear balance, perception is seldom an incapacitating injury after an explosive detonation.

The balance and position organ (semicircular canal system) is analogous to the hearing organ in three important ways: (1) both are encased in bone; (2) balance and hearing organs are within millimeters of each other; and (3) both have delicate sensory cells necessary for nerve transmission.

Figure 1A:
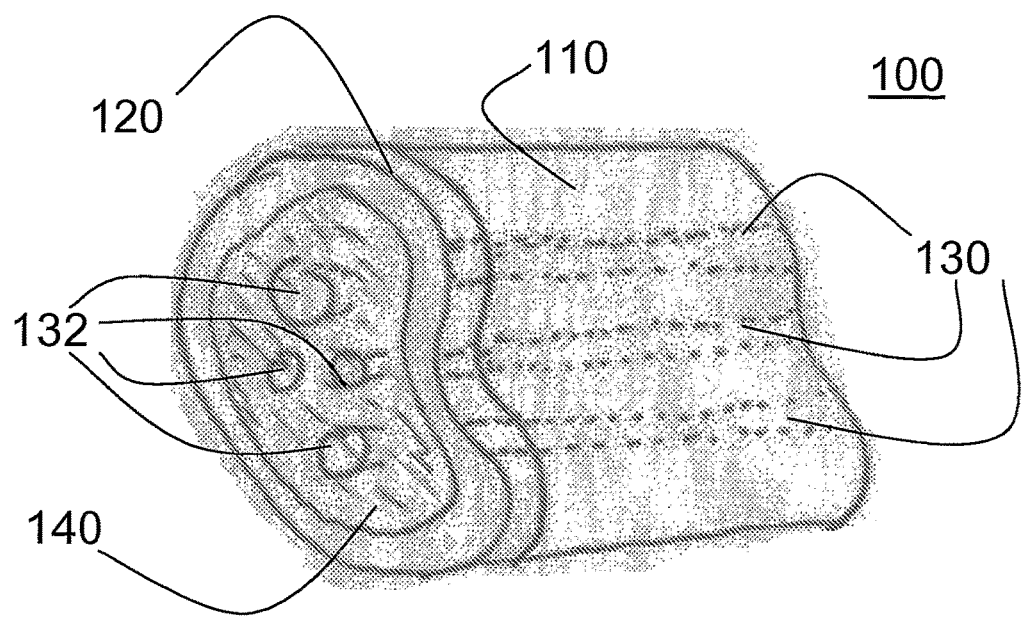
FIG. 1(a) is a perspective view of a hearing loss prevention device in accordance with a preferred embodiment of the present invention.
Figure 1B:
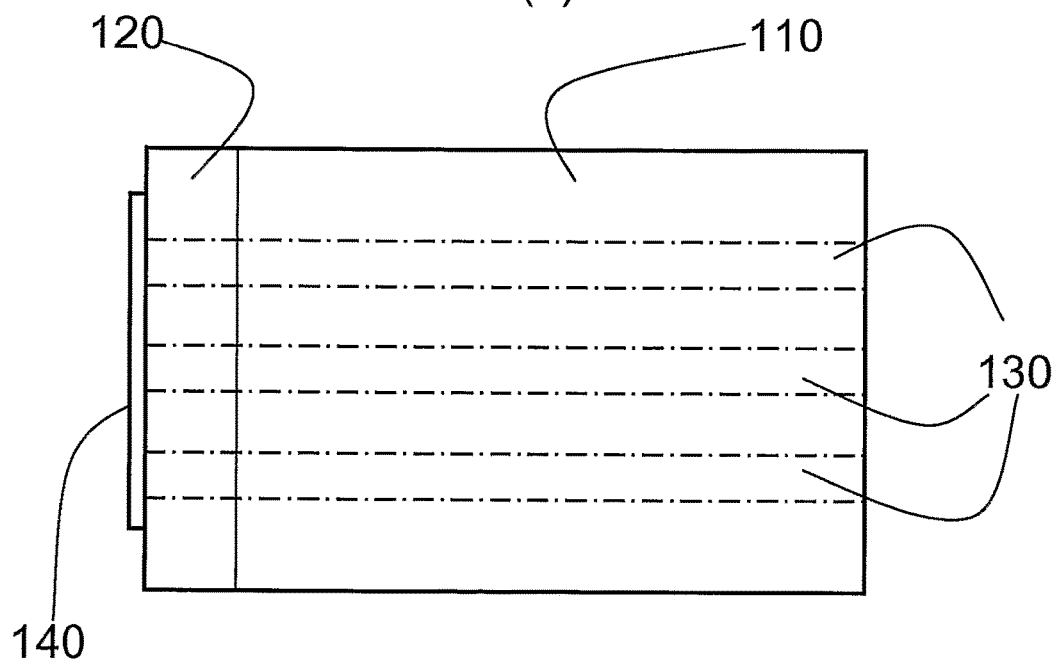
FIG. 1(b) is a side view of the hearing loss prevention device of FIG. 1(a) in accordance with a preferred embodiment of the present invention.

A first preferred embodiment of a hearing loss prevention device 100 in accordance with the present invention is described with reference to FIGS. 1(a) and 1(b). This embodiment also might be referred to as an acoustic isolator assembly. In FIGS. 1(a)-(b), a perspective view and a side view of an acoustic isolator assembly for placement within an ear canal is shown. A body 110 preferably made of a soft compliant material is provided with a plurality of channels 130 extending therethrough. Channels may be for example, sound-transmitting polymer tubes. The body 110 preferably is shaped to fit into an ear canal. The shape of the body 110 may be, for example, cylindrical. An acoustically limp material 120 forming a distinct component layer is connected, secured or attached to an end of the body 110. The plurality of channels 130 extend through the acoustically limp material 120. A component appearing as a film or disc 140, made for example with a high strength polymer, such as mylar, is placed or secured over an end of the acoustically limp material 120 to thereby cover or seal the openings 132 of the channels 130. The film or disc 140 may be flat or contoured and may have a thickness ranging up to approximately ten micrometers. The film or disc 140 in operation preferably is in direct contact with the end of the acoustically limp material 120. Preferably, the film or disc 140 seals the openings 132 of the channels. The component, film or disc 140 alternatively may be attached on one side to form a flap that closes in response to high intensity sound energy. In such alternate embodiments, closure is passive and results from the physical force of the sound energy, which acts to push the flap shut, closed or sealed against the component.

The shock wave intercepting film or disc 140 must simultaneously satisfy two criteria: It must be sufficiently thin such that it does not interfere with ambient sound transmission, and it must be sufficiently strong that it does not rupture when subject to overpressures of one or two atmospheres. Modeling efforts indicate that a microns-thick film of one of the commercially-available high-strength polymers can meet these two requirements. Specifically, the mass/area of the 10-micron film is sufficiently low as to have little influence on normal sound transmission. With adjusted radius it is capable of withstanding overpressures of 2 (or more) atmospheres. The essential mechanism of the protection afforded by the film (and ear plug seal) is the blockage of significant airflow through the ear canal thereby maintaining pressures at the tympanic film, at levels representing a small fraction of the outer overpressure, and thus minimizing the subsequent destructive forces transmitted via the ossicles of the middle ear to the oval window of the cochlea. Key to understanding this function is the realization that a doubling of the pressure in the ear (corresponding to an over pressure of one atmosphere) requires an approximate doubling of the mass of air in the inner ear. Thus, if the plug/film system can block the mass flow of air resulting from a step-function of immediate pressure increase through the ear canal, without impeding the extraordinarily small amounts of air flow associated with sound transmission, it can effectively protect the inner ear against significant overpressures.

Three results relevant to selecting the thickness and properties of the film to cover the sound channel are presented. First, the result of a one-dimensional analysis of the effect of a film of mass density, $\rho_m$, and thickness, t, on the transmission of sound waves through the film. In this estimate, the film is taken to be unsupported (see following paragraph for the effect of the support) and free to oscillate—only its mass impedes the transmission of waves. Consider incident sound waves in air of frequency, $\omega$, and pressure amplitude, $p_I$, "blocked" by the film. Let $p_T$ be the pressure amplitude of the waves transmitted through the film into the air on the other side of the film. A classical analysis of the relation of the transmitted pressure amplitude to the incident amplitude gives $$\frac{p_T}{p_I} = \frac{1}{1 + \frac{\omega \rho_m t}{2\rho_{air} c_{air}}}$$

where and are the density and speed of sound in air. For polymeric films ($\rho_m \sim 10^3$ kg/m$^3$) with thicknesses in the range of t~1-10 μm, the transmitted wave will be essentially unaltered by the film for frequencies below $\omega \sim ^4 s^{-1}$.

The above estimate ignores the fact that the film will be firmly attached around the edge of the channel through the ear plug. Now consider regard the film as a circular clamped plate of radius R, corresponding to the radius of the channel. The lowest vibration frequency of the plate is $$\omega_c = \frac{10.21}{R^2} \sqrt{\frac{E_m t^3}{12(1 - v_m^2)}}$$

where and are the Young's modulus and Poisson's ratio of the film. For polymeric films of 1 radius and thicknesses on the order of t~10 μm the lowest vibration frequency is on the order of $10^4 s^{-1}$. If R=2 mm, the lowest frequency is reduced by a factor of four. The implication of the two results outlined above is that the film will respond quasi-statically to sound waves with frequency less than $10^3 s^{-1}$.

The most restrictive constraint on the design is the requirement that the film not restrict the amplitude of the sound waves in the channel. The amplitude of the air particle motion, $\delta$, in a sound wave is related to the amplitude of the pressure, $p_1$, by $$\frac{\delta}{p_I} = \frac{1}{\rho_{air} c_{air} \omega}$$

When subject to a pressure $p_1$ a clamped circular film experiences a deflection, $\delta_{membrane}$, given by (based on a quasi-static estimate, c.f. above)

$$\frac{\delta_{membrane}}{p_I} = \frac{3(1 - v_m^2)R^4}{16 E t^3}$$

To avoid reduction of sound transmission to the inner ear, the film deflection should not be significantly less than the amplitude, $\delta$, of the particle motion. A film with radius 1 mm and thickness greater than 10 μm does not meet this requirement, but a film with thickness 1 μm easily does. A film with thickness 2 μm is currently considered to be optimum, while a film of thickness of about 6 μm meets the requirement sufficiently to provide protection from blast overpressure without substantially reducing normal hearing. Experimentation with sound transmission as a function of the film thickness will establish that the quality of hearing is not significantly reduced by the film.

Can a circular polymeric film of thickness of order t~1-10 μm and radius R~1 mm block an over-pressure, Δp, of an atmosphere or more? Two estimates that show that a well-selected film material can survive these over-pressures based on the two most likely failure modes. First, consider shear-off at the perimeter of the film. Elementary equilibrium requires that the shear strength, $\tau_m$, of the film must be such that $$\tau_m \rangle \frac{R}{2t} \Delta p$$

Thin film polymeric materials exist whose shear strength is adequate (~50 MPa) to ensure survival of films even as thin as 1 μm to survive an over-pressure of an atmosphere (0.1 MPa). Next, consider tensile tearing of the film at it perimeter. In this case the tensile strength of the film, $\sigma_m$, must satisfy $$\sigma_m \rangle \frac{R}{2t \sin \alpha} \Delta p$$

where $\alpha$ is the deflection angle of the film at the perimeter. Assuming moderate ductility, a film should be able sustain deflection angles on the order of $\alpha \sim 30°$. For this failure mode, as well, there is a selection of thin film materials that can survive over-pressures of several atmospheres for thicknesses on the order of 1 μm or more.

Viscous effects on the propagation of pressure pulses: In the simplest cases of sound propagation it is sufficient to solve the wave equation in the geometry of interest. For example, when amplitudes are small, any arbitrary signal can be represented as a Fourier series, and each Fourier mode (frequency $\omega$) propagates with the wave (sound) speed c. The wave length of the propagating signal is then $\lambda = c/\omega$.

Viscous effects in the gas damp the wave propagation. The effect of viscosity is always present near rigid boundaries since the no-slip boundary condition demands that the fluid speed tangent to the surface equals zero at a stationary rigid wall. This viscous damping is, of course, unwanted if there is only to be limited sound attenuation (either noise or a spoken command).

To estimate the viscous effects it is simply necessary to note that in any oscillatory fluid flow (small amplitude sound signals correspond to oscillatory fluid motions) there is a narrow region—a boundary layer—near the rigid surface where viscous effects are typically confined. The thickness of the layer $\delta$ is approximately $(\nu/\omega)^{1/2}$, where $\nu$ is the kinematic viscosity of the fluid. Consequently, for sound propagation through a narrow constriction of width W, we should expect viscous effects to be negligible so long as $\delta = (\nu/\omega)^{1/2} < W$. For air at room temperature and pressure, $\nu = 10^{-5}$ m$^2$/sec. For a typical audio frequency of 1000 Hz, the boundary-layer thickness is about 100 micrometers, which is about the thickness of a human hair.

Figure 2A:
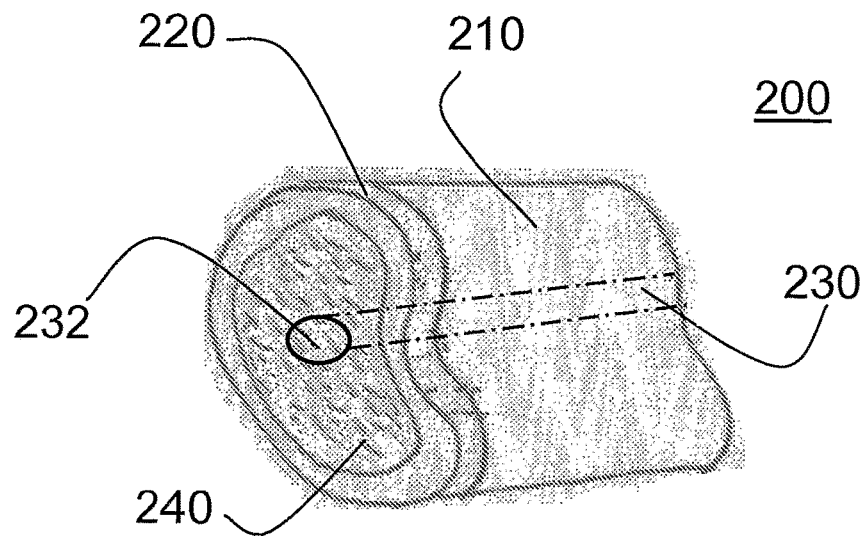
FIG. 2(a) is a perspective view of a hearing loss prevention device in accordance with an alternative preferred embodiment of the present invention.
Figure 2B:
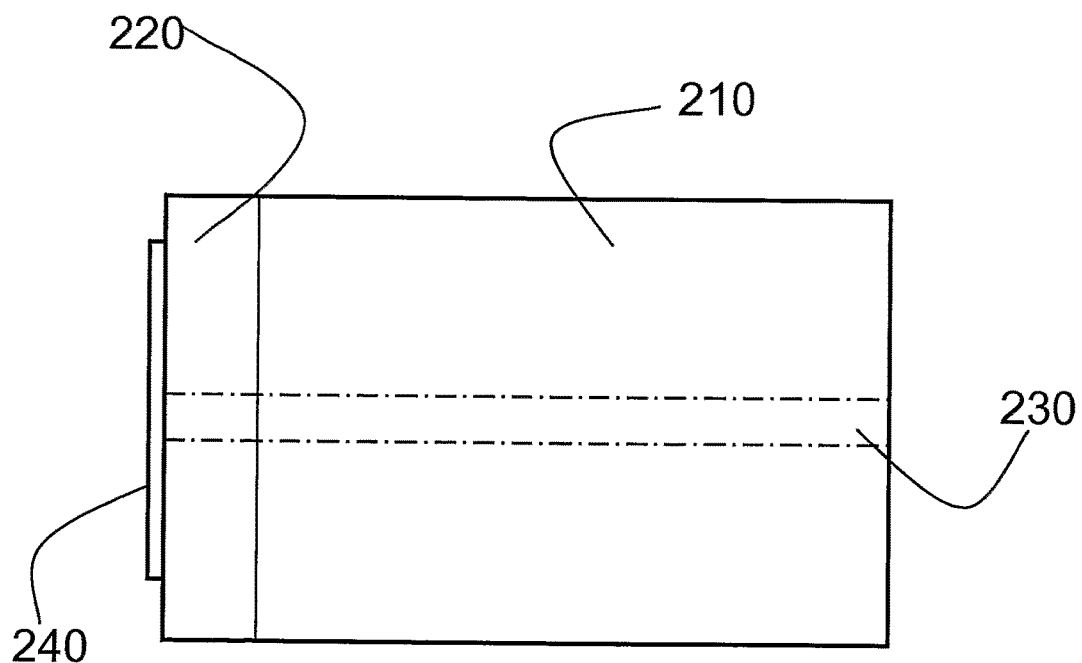
FIG. 2(b) is a side view of the hearing loss prevention device of FIG. 2(a) in accordance with a preferred embodiment of the present invention.

A second preferred embodiment of a hearing loss prevention device 200 in accordance with the present invention is described with reference to FIGS. 2(*a*) and (*b*). This embodiment likewise might be referred to as an acoustic isolator assembly. In FIGS. 2(a)-(b), a perspective view and a side view of an acoustic isolator assembly for placement within an ear canal is shown. A body 210 preferably made of a soft compliant material is provided with a single channel 230 extending therethrough. The body 210 preferably is shaped to fit into an ear canal. The shape of the body 210 may be, for example, cylindrical. An acoustically limp material 220 is connected, secured or attached to an end of the body 210. The channel 230 extends through the acoustically limp material 220. A film or disc 240, made for example with a high strength polymer is placed or secured over an end of the acoustically limp material 220 to thereby cover or seal the openings 232 of the channels 230. The film or disc 240 may be flat or contoured and may have a thickness ranging from a few micrometers to several tenths of micrometers. The film or disc 240 preferably is in direct contact with the end of the acoustically limp material 220.

The device in accordance with the present invention will selectively intercept and reflect shock wave energy into a direction perpendicular to the ear canal by utilizing a sound-transmitting tube or tubes 130, 230 with a high-strength film 140, 240 covering the outer opening(s) 132, 232. The tube(s) 130, 230 will be surrounded by high-density, acoustically limp, material 120, 220 and will be inserted into the external auditory canal. The film 140, 240 will reflect high-energy acoustic waves, but will be transparent to low intensity sound waves for normal hearing, and ambient sounds.

The high-strength polymer film 140, 240, on the order of several microns in thickness, and capable of reflecting high-energy acoustic waves, covers one or more small-radius hole(s) designed to allow innocuous sound transmission required for front-line communication. The assembly will be fully encased in compliant medical grade silicone 150, 250 and be inserted into the ear canal at or near the cartilaginous/bony interface.

In operation, the shock wave intercepting film 140, 240 must simultaneously satisfy two essential criteria: It must be sufficiently thin such that it does not interfere with sound transmission, and it must be sufficiently strong that it does not rupture when subject to overpressures of one or two atmospheres. Modeling efforts indicate that a microns thick film of one of the commercially-available high-strength polymer can meet these two requirements. Specifically, the mass/area of the 10-micron film is sufficiently low as to have little influence on sound transmission. With adjusted radius it is capable of withstanding overpressures of 2 (or more) atmospheres. The essential mechanism of the protection afforded by the film (and ear plug seal) is the blockage of significant airflow through the ear canal thereby maintaining pressures at the tympanic membrane, at levels representing a small fraction of the outer overpressure, and thus minimize the subsequent destructive forces transmitted via the ossicles of the middle ear to the oval window of the cochlea. To appreciate this effect, one must realize that an overpressure of two atmospheres would require roughly an instantaneous doubling of the mass of air within the ear canal region. Thus, if the plug/thin film system can block the mass flow of air resulting from a step-function of immediate pressure increase through the ear canal (without impeding the extraordinarily small amounts of air flow associated with sound transmission), it can effectively protect the inner ear against significant overpressures.

While some of the embodiments of the present invention have been described in the military context, it should be understood that all of the embodiments are applicable to many circumstances or settings other than military settings.

In a third preferred embodiment of the present invention, a concept that may be referred to as "vacuum interposition" is employed. Generally speaking, the embodiment uses hearing protective technology consisting of silicone rubber-covered sealed cavities containing micro circuitry adapted from affixed to ends of a vacuum chamber in the ear canal.

Figure 3:
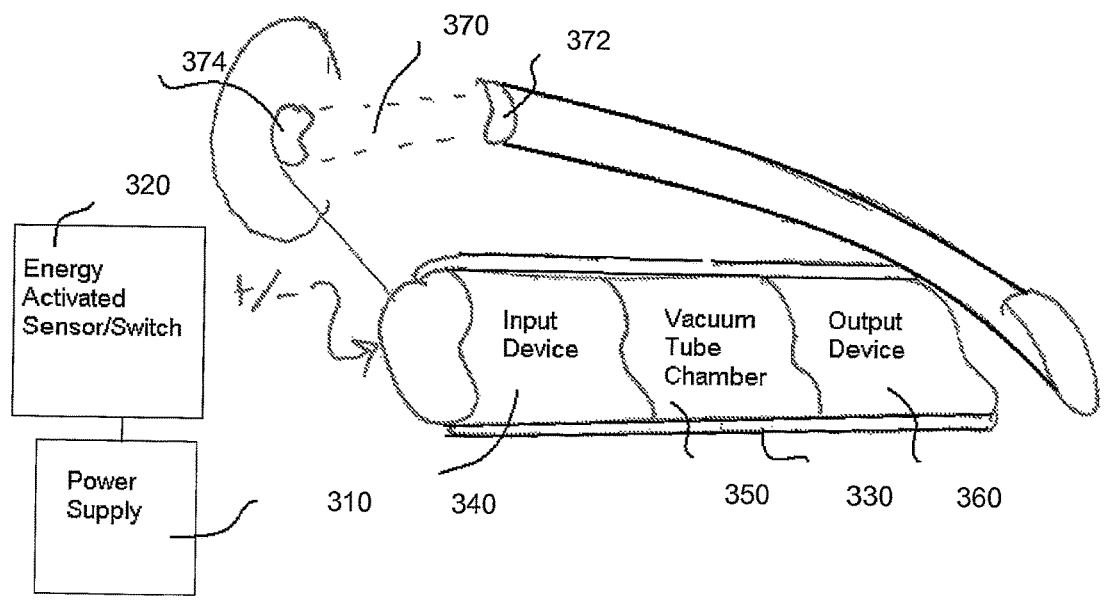
FIG. 3 is a diagram of a device constructed in accordance with a third preferred embodiment of the present invention.
Figure 4:
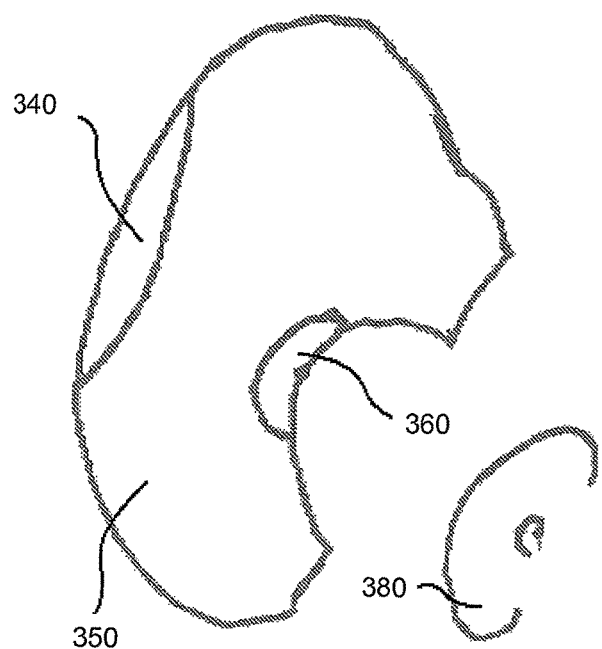
FIG. 4 is a diagram of an alternate arrangement of the third embodiment of the present invention.

As shown in FIG. 3, the third preferred embodiment of the invention has a power supply 310, an energy activated sensor or switch 320, and a silicon membrane 330 having within it an input device or receiver 340, a vacuum tube chamber 350, and an output device or transmitter 360. The energy activated sensor or switch may be of any of a variety of structure or arrangements, two of which are discussed below with reference to FIG. 15 and FIGS. 16(a) and (b). The energy activated sensor has a response time interval, for example, of less than 30 microseconds. Other response times may be appropriate and useful under various circumstances and the present invention is not limited to any particular sensor or switch or any particular response time.

The input device 340 has circuitry or other means (not shown) for conducting or transmitting signals through the device. The signals may be conducted or transmitted through the device by any means, for example, by photonic through the vacuum, electrical wired or RF-energy wired. The output device 360 receives signals from the input device and transduces sound to the ear drum.

The device may be designed to transmit sounds in a particular frequency range. For example, frequencies in the range (500 to 4,000 Hz) of verbal commands and sounds found in the immediate surrounding may be transmitted by wired, electromagnetic or laser transmitted photonic energy through a vacuum chamber to a receiver adjacent to the ear drum. If electromagnetic broadcast is utilized, the effective transmission range of transmitter 360 would be less than 10 cm enabling redundant contralateral hearing should systems failure occur on one side. The energy activated sensor or switch 320 will respond to incoming sonic blast(s) and turn off the sound transmission component of the device. To limit hearing damage, switch response time will be less than 1 millisecond, with approximately 30 microseconds attained. Reset time interval will be less than 30 microseconds. To prevent interception, the transmitter 360 and receiver 340 may be paired using, for example, prime number encryption. The present invention is not limited to encrypted signals or any particular type of encrypted signals.

The embodiment further may have different settings, adjusted by changing the sensitivity of the device or the sensors for various circumstances, whether the context be military, industrial or otherwise. For example, in military settings, three decibel (dB) tolerance settings could be used: (1) sleeping quarters; (2) recreational area; and (3) mess hall to accommodate ambient noise. Fewer or greater tolerance settings may be provided with the present invention. Operational settings could feature combat mode, transport mode (trucks, Humvees, helicopters), and quiet (reconnaissance) mode. An alternate approach for this preferred embodiment is to use microfabricated quantum cascade lasers to transmit photonic "sounds" through the vacuum.

In FIG. 3, the device is shown as being constructed to be inserted into an ear canal between an ear drum 372 and an ear canal opening 374. Such a device preferably is designed such that the silicone membrane 330 fits tight in a typical ear canal. In an alternate arrangement, a device in accordance with this third embodiment may be constructed to fit over an ear 380 like an ear muff. Many other arrangements of this third embodiment of the invention, such as being part of a head band, helmet, hat, head or body container or the like are possible and will be apparent to one of ordinary skill in the art.

A fourth preferred embodiment will be described with reference to FIGS. 5-8. Preliminarily, it is known that infants with ear canal wall atresia with an intact inner ear register a 90 dB hearing loss. Using this knowledge, the fourth embodiment of the present invention takes advantage of physical properties of advanced polymer gel chemistries and nanoscale structures to protect the hearing organ from incoming pressure forces by forming "instant bone" in the ear canal that simulates an atretic ear.

The ear canal is the most vulnerable point of entry into the hearing organ for damaging sound waves. The human body has already supplied evidence for the protective nature of bone. The only organ fully encased in bone is the vestibular system, known to contain the body's balance and position receptors. Even though the semicircular canals are only millimeters away from the hearing organ and have delicate sensory cells similar to the loss of cochlear balance, perception is seldom an incapacitating injury after an explosive detonation.

The balance and position organ (semicircular canal system) is analogous to the hearing organ in three important ways: (1) both are encased in bone; (2) balance and hearing organs are within millimeters of each other; and (3) both have delicate sensory cells necessary for nerve transmission.

Figure 5A:
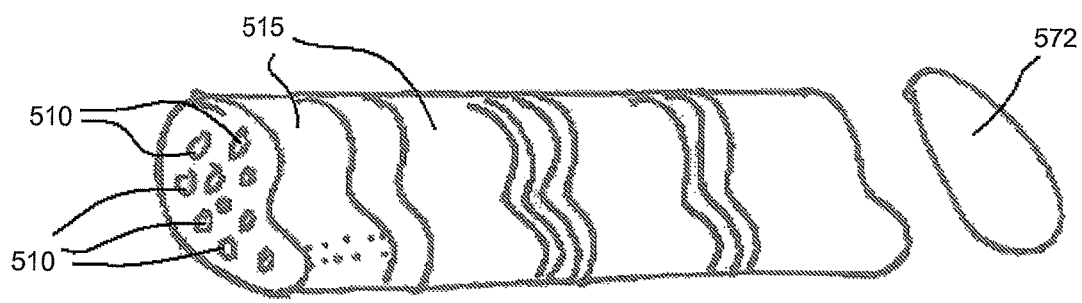
FIG. 5(a) is a perspective view of a device in accordance with a fourth preferred embodiment of the present invention.

In FIGS. 5(a) and (b), a perspective view and a cross-section of an acoustic isolator assembly for placement within an ear canal is shown. A plurality of sound transmitting polymer tubes 510 run through gel or fluid-filled spacers 515 that are delimited by paired bi-concave discs 530, 540 interspaced with a gel with a high spring constant. The gel spacers 515 may have peripheral grooves on their outer surfaces to give the acoustic isolator assembly shape filling capacity and some reserve capacity to fit into an ear snugly upon expansion or activation. Small discs 530 contain nanoparticles 710 and elastic micro balloons 720 of a higher density than the gel in the spacers. The discs 530, 540 preferably are formed from a hard sound reflecting material. The discs may be shaped, for example, like a snail operculum as shown in FIGS. 6(a) and (b) and are flat plates, bi-concave, convex/concave or bi-convex. The acoustic isolator assembly is covered with a silicone membrane 550.

Figure 5B:
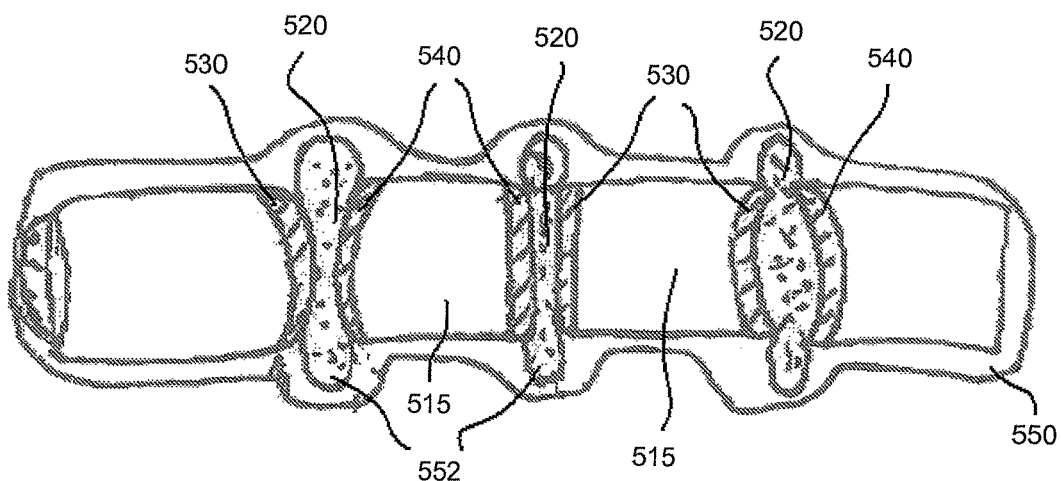
FIG. 5(b) is a side and cross sectional view of a device in accordance with a fourth preferred embodiment of the present invention.
Figure 7C:
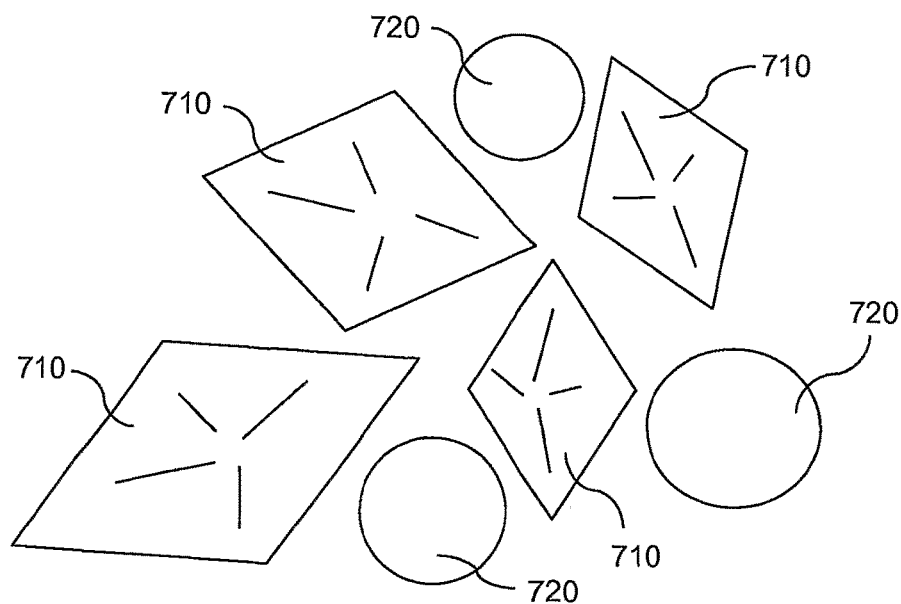
FIGS. 7(c) and (d) are diagrams illustrating the operation of nanoparticles in the fourth preferred embodiment of the present invention.
Figure 7D:
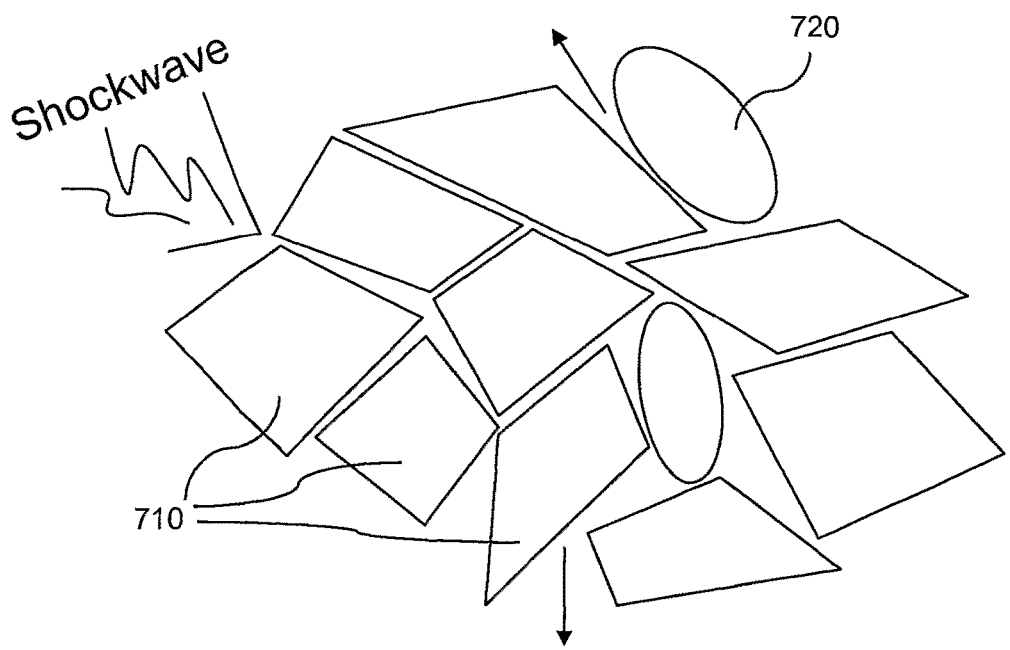
FIGS. 7(a) and (b) are top and side views illustrating the second structure of a disc-shape bag filled with nanoparticles intended to be a sound absorber forming a portion of the fourth embodiment of the invention.

The acoustic isolator assembly of this fourth embodiment instantaneously responds to abrupt changes in sonic pressure to form into a material with bone-like consistency in the ear canal, closing sound conducting channels 212 in energy ranges from 500 to 10,000 Hz, such as those found in the range of verbal commands and the immediate operational surroundings. All sounds are transmitted from the outer ear region to the ear drum 572 through a gel/nanoparticle matrix. The gel 520 is designed to attenuate the transmission of energy at levels known to damage the hearing organ. As shown in FIG. 5, the incoming pressure wave impacts the outer disc 530 displacing this disc inward toward the ear canal. The pair of biconcave discs 530, 540 is compressed from the sonic energy squeezing fluid in the gel spaces 515 into the silicon membrane 552 as shown in FIG. 5. The residual shock energy passes through the subjacent rubberlike gel spaces 515 to the next biconcave disc pair 530, 540 compressing into each gel-nanoparticle structure in sequence until the all complex power levels of sound have been attenuated. The outer silicone rubber membrane 550 acts as a reservoir for the displaced fluid and nanoparticles from the inner cylindrical device. The spring constant of the gel 520 is tuned to recoil and rebound in less then 30 microseconds. As shown in FIGS. 7(a), 7(b) and 7(d), when the gel spaces 515 are compressed, the nanoparticles compact together to form a bonelike structure. In this manner, the gel absorbs energy and the compacted nanoparticles conduct sound to an angle orthogonal to the long axis of the ear canal. Since the fourth embodiment preferably is constructed of passive components, to energy activation sensor or switch is necessary, although variations using or requiring such a sensor or switch will be apparent to those of skill in the art and fall within the scope of the invention.

As shown in FIGS. 7(a), 7(b) and 7(d), when the gel spaces 515 are compressed, the nanoparticles compact together to form a bonelike structure. In this manner, the gel absorbs energy and the compacted nanoparticles conduct sound to an angle orthogonal to the long axis of the ear canal. Since the fourth embodiment preferably is constructed of passive components, to energy activation sensor or switch is necessary, although variations using or requiring such a sensor or switch will be apparent to those of skill in the art and fall within the scope of the invention.

Figure 8:
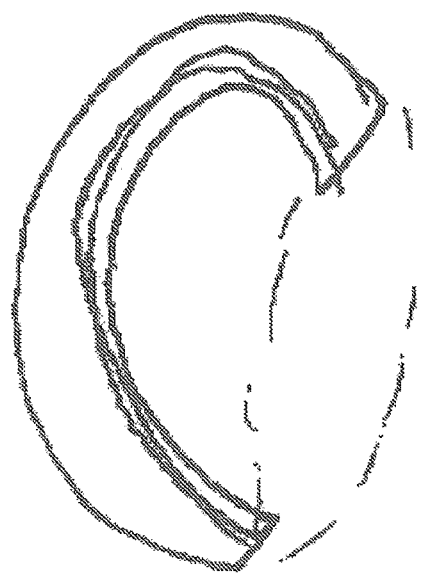
FIG. 8 is a diagram of an alternate arrangement for placement of a device in accordance with the fourth embodiment of the present invention adjacent a person's ear.

While the fourth embodiment in shown in FIGS. 5-6 as being a device that is placed in the ear canal, one of skill in the art will recognize that many alternatives exist, such as incorporating the fourth embodiment into an ear muff design such as is shown in FIG. 8 or another design outside the ear canal.

A fifth preferred embodiment of the invention is described with reference to FIGS. 9-12. This fourth preferred embodiment of the invention selectively reflects acoustic waves by utilizing nanoparticles with dipole moments that can electromagnetically re-orient to form acoustic wave deflector surfaces or nanoperforations.

Figure 9:
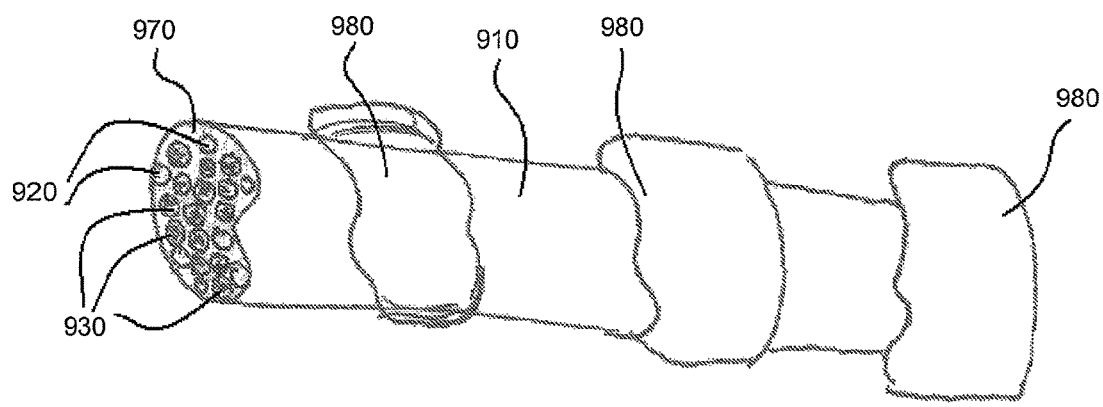
FIG. 9 is a diagram of a fifth embodiment of the present invention.
Figure 10:
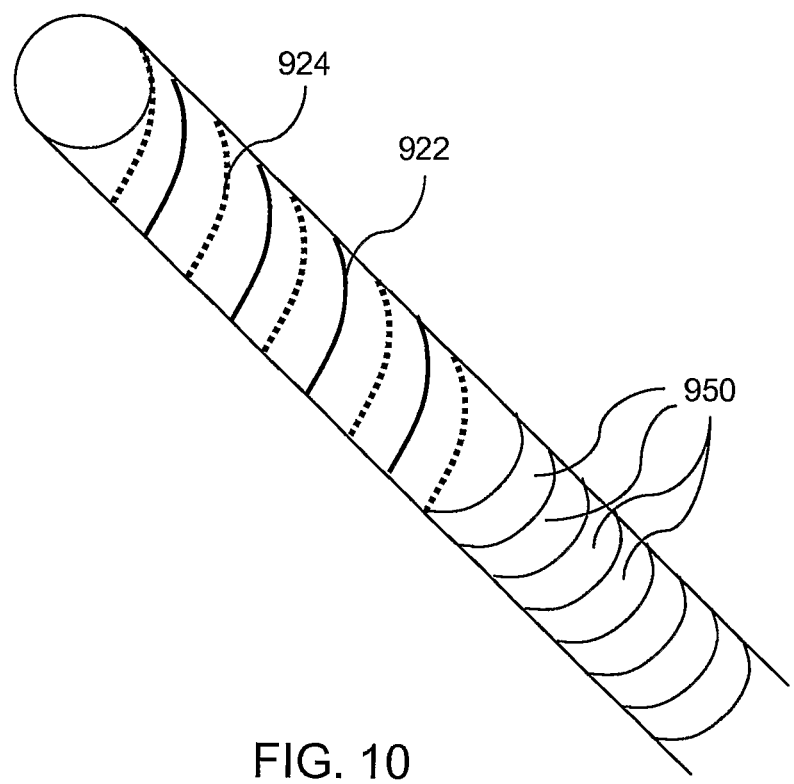
FIG. 10 is a diagram of tube in accordance with a fifth embodiment of the present invention.
Figure 11:
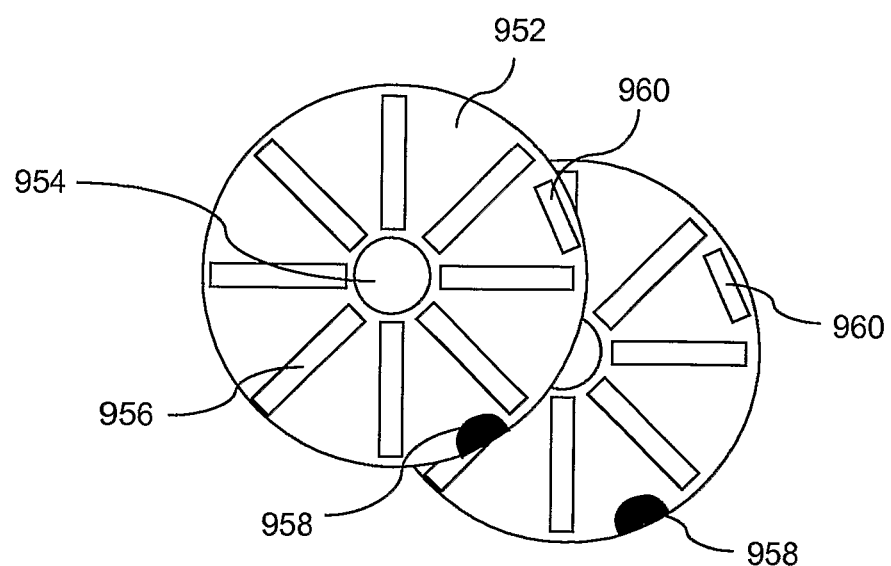
FIG. 11 is a diagram illustrating the structure of discs in accordance with a fifth embodiment of the present invention.

As shown in FIG. 9, a cylindrical shaped container 910 with polymer microtubes 920, 930 running along the long axis of the container 910 fits within a person's ear canal 370 between the ear drum 372 and the opening 374. The microtubes 920, 930 are, for example, on the order of 10 to 100 microns in diameter nm. The microtubes may be composed of soft and compliant polymer with tiny ferrous rings or ridges along their circumference. The microtubes 920 are empty to allow ambient sound transmission while the microtubes 930 are filled with stacked discs 950 as shown in FIGS. 10-11. The unfilled tubes will collapse and close upon sound energy deformation of the assemblies, or will remain open depending on the sensitivity and operational mode of the device. Each of the microtubes 930 is wound with an alignment field coil 922 and a disalignment field coil 924. Alternatively, the microtubes 930 may have built into them a conductive series of rings or tracks. Preferably the discs 950 are made of a material with bone-like density and sound reflecting and/or absorbing characteristics.

Each disc 950 has a body 952 with a spindle hole 954 and a plurality of sound apertures 956 formed within in it, for example, constructed by microlithography. A short microfabricated column or wire extends through the spindle holes in the discs in the stack. Each disc further has a magnetic alignment pad 958 and a magnetic disalignment pad 960. An intertubular ground substance 970 of highly elastic, gel encases the microtube array. As with the prior embodiments of the invention, this embodiment may take on other forms such as a covering wrapping around the outer aspect of an ear.

Figure 12:
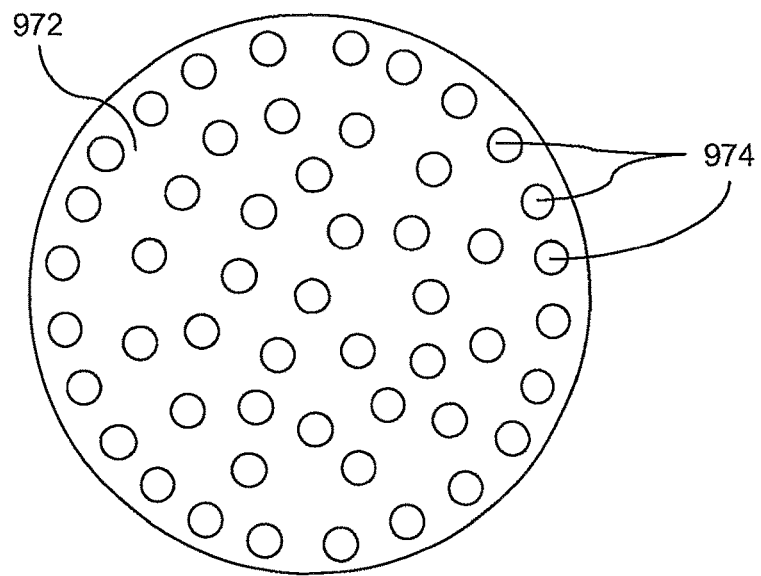
FIG. 12 is an example of a perforated nanoparticle with coating such as magnetizable metal in accordance with the fifth embodiment of the present invention.

While FIG. 11 depicts nanodiscs, other types of nanoparticles such as rods, rectangles, trapezoids, or irregular discs may be used. For example, the microtubes may be filled with sound attenuating nanodiscs such as are shown in FIG. 12. The nanodisc shown in FIG. 12 is made of or coated with sound damping materials 972 and has a plurality of nanoperforations 974 that are, for example, 10 nm holes. Alternatively or additionally, the nanodisc of FIG. 12 may have surface-raised nanobumps. Many alternatives will apparent to those of ordinary skill in the art.

Variations of this embodiment additionally may be used to produce a protective shield or coating to protect body cavities from high velocity sound waves traversing beyond the end of travel for a projectile such as a bullet entrapped by a protective vest. This layer would be considered a sound aperture beneath the body armor itself. Activation would be in the form of a switch or local impact with realignment of the nanoparticles due to magnetic field.

Figure 15:
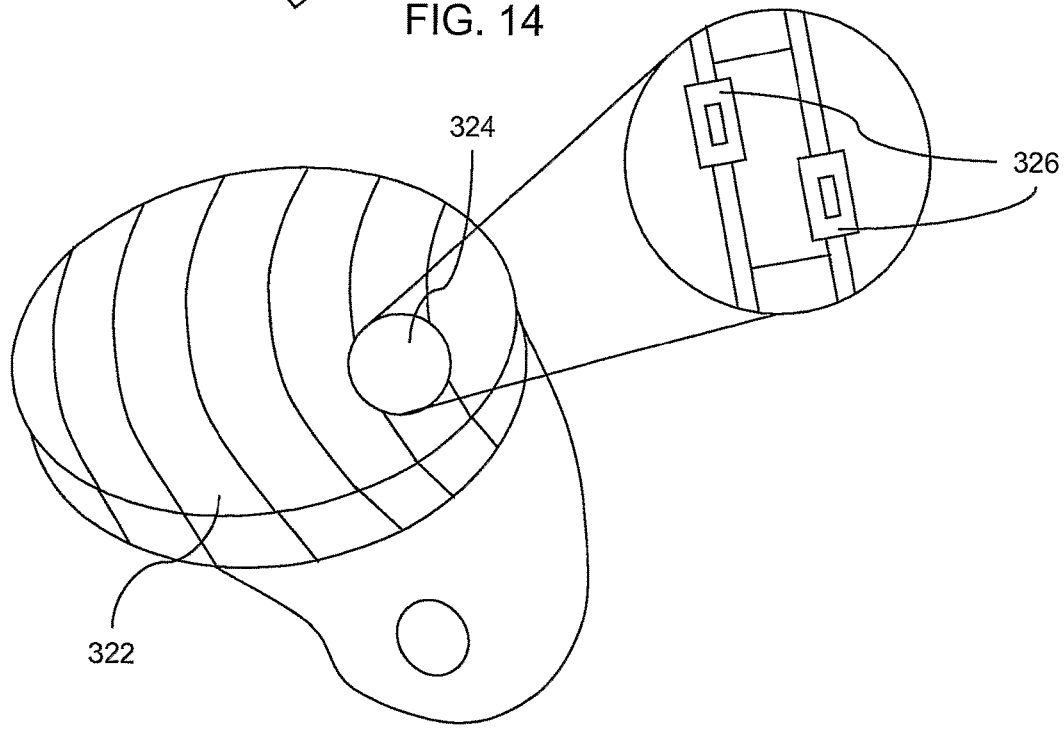
FIG. 15 is a diagram of a photonic energy activated switch in accordance with a preferred embodiment of the invention.

A pressure sensitive/shock-wave activated switch turns such as is shown in FIGS. 15-16 and discussed below turns on EMF generating coils 980, which in turn align the discs 950 to become sound deflecting surfaces, re-orienting acoustic energy perpendicular to the long axis of the ear canal. During reception of an acoustic shock wave, the filled tubes may be displaced perpendicular to their length, thereby collapsing or limiting sound transmission through the empty tubes. The container 910 has three coils 980 on its circumference, capable of generating up to a 1 tesla Electromagnetic Field. The device will reverse EMF polarity to disalign the discs. While rotating discs are described in this embodiment, other designs for nanoparticles such as the following are possible: split log, cylinder, trapezoid, rhombus, square, complex rectangles, discoid, oval. A possible drawback of this preferred embodiment is that it will block some ambient sound even when not activated.

A sixth preferred embodiment of the present invention is based on research showing that outer hair cells can be electrically stimulated in vitro. Electro stimulatory inhibition of cochlea sensory cells is used in the sixth preferred embodiment to dampen sound energy transmitted along the tectoral membrane in the inner ear. The device will hyperpolarize outer hair cells, attenuates the mechanical transduction of sound energy onto the tectoral membrane. The net effect is to render outer hair cells of the cochlea refractory to sound energy input.

Figure 13:
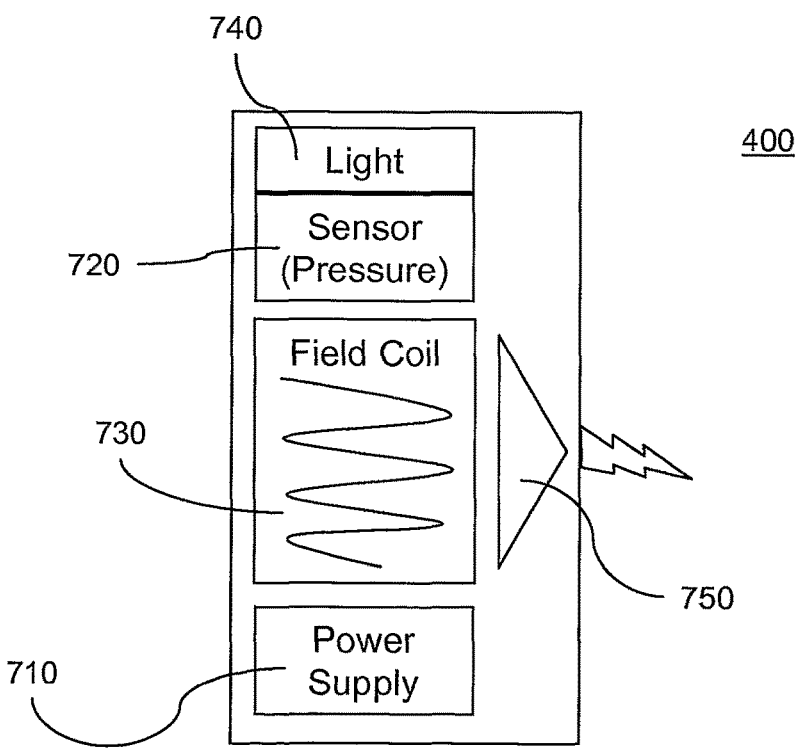
FIG. 13 is a diagram of a device in accordance with a sixth preferred embodiment of the present invention.
Figure 14:
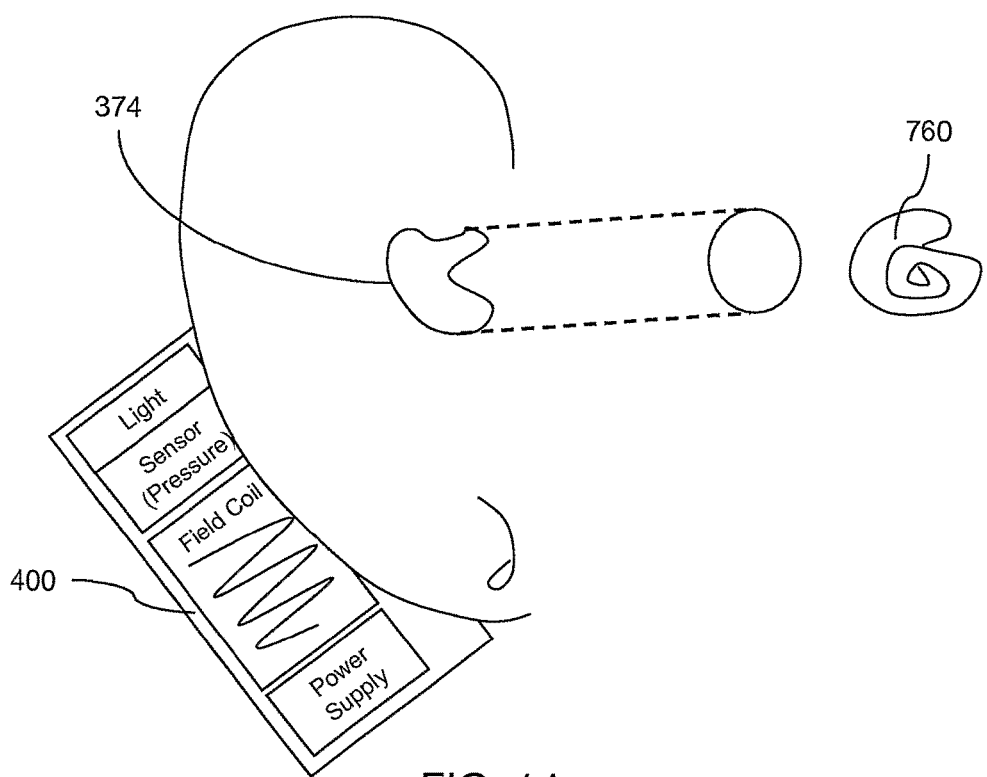
FIG. 14 is a diagram illustrating the placement of a device in accordance with the sixth preferred embodiment of the present invention.

As shown in FIGS. 13-14, an ear patch 400 affixed to the skin or outer ear 376 contains a power source 710, a sound pressure-sensitive switch 720, an electromagnetic field (EMF) generating coil 730, a light sensor 740 and an antenna 750. The device may be in the form of an ear patch worn on the outer ear as is shown in FIGS. 13-14, or may project from the inner aspect of for example, a helmet to abut the mastoid region of the skull. Another design calls for a field coil antenna, inserted into the ear canal in front of the third, fourth or fifth embodiments of the present invention to be pointed to the cochlea 760 but not the vestibular apparatus, the balance and position sensing organ.

In this sixth embodiment, a pressure sensitive/shock-wave activated switch turns on EMF generating coils 730, which in turn hyperpolarize (paralyze) the outer hair sensory cells in the cochlea, preventing them from activating or transducing sound. It is known that the protein prestin in the hair cells are contractile (Anders Fridberger, 2004) which converts receptor potentials into fast alterations of cellular length and stiffness that routinely boost hearing sensitivity almost one thousand fold. The device will stop EMF transmission as the blast shock wave(s) are no longer encountered.

In this sixth embodiment, the device will interfere with hearing until the action potential of the hyperstimulated outer hair cells return to normal resting state Alignment of the antenna is important. The device may use a reflected light signal or the like to point an EMF antenna 750 to the inferior aspect of the umbo of the mallius bone of the middle ear.

FIG. 15 shows an embodiment of a photonic energy activated switch that may be used in connection with various embodiments of the present invention. The switch may have a housing 322 and a plurality 324 of small (approximately 100 microns) light sensing diodes in the far red to infrared spectrum. The diodes 326 wired in parallel or in series. The housing 322 may be of any appropriate shape, form or material to operate with any of the embodiments discussed above.

Figure 16A:
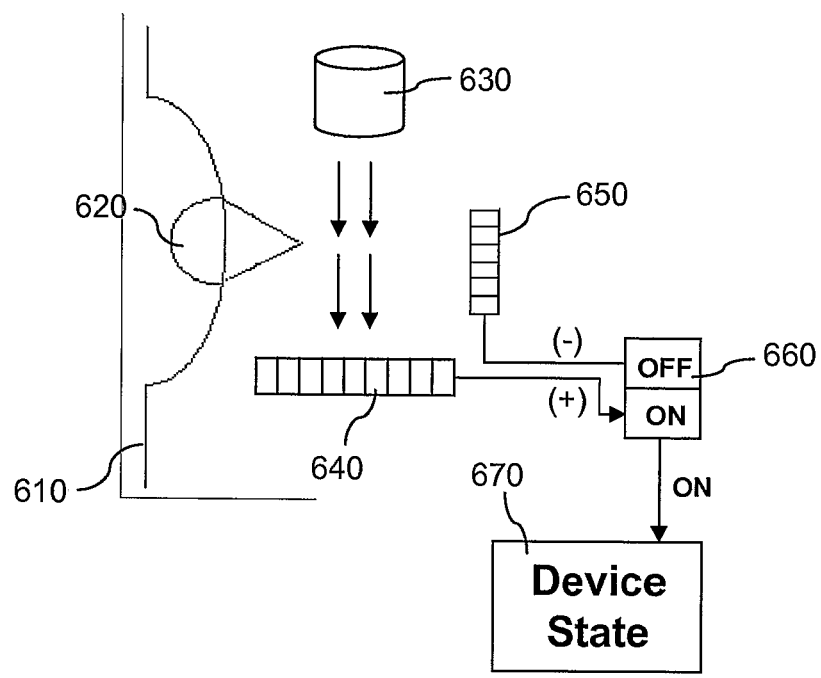
FIGS. 16(a) and (b) are diagrams of a sound energy activated switch in accordance with a preferred embodiment of the invention.
Figure 16B:
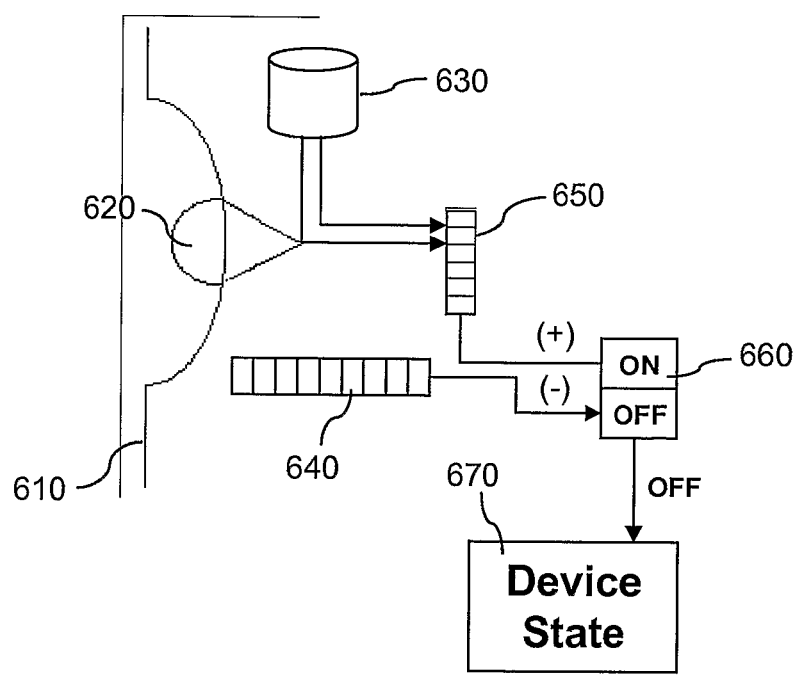

Alternatively, FIGS. 16(a) and (b) illustrate a sound energy activated switch that may be used in connection with various embodiments of the present invention. The sound energy activated switch. FIG. 16(a) illustrates the switch in a position corresponding to an ON device state 670. FIG. 16(b) illustrates the switch in a position corresponding to an OFF device state. A mirrored cone 620 is located in a membrane610. Two arrays 640 and 650 of diode photodetectors are arranged perpendicular to each other with one array 640 aligned with an LED 630 and the other array 640 aligned perpendicular to the LED 630. The LED may, for example, be approximately 300 microns in diameter. The outputs of the arrays 640 and 650 are connected to a switch 660. The membrane and cone are aligned relative to the diode arrays and the LED such that under normal conditions, the mirrored cone 620 does not interfere with the reception of light from the LED at the array 640, but when a noise or shock wave displaces the membrane, the mirrored cone redirects the light from the LED 630 onto array 640, thereby changing the state of the device from ON to OFF. When the shock wave dissipates, the membrane and hence the cone return to their original positions, thereby permitting light form the LED to again be received by array 640, thereby returning the device to an OFF state. Tension of the membrane 610 may be adjustable for sensitivity and different operational modes. Various types of switches may be used for switch 660 and various arrangements of the diodes and mirrored cone will be apparent to those of skill in the art. Additionally, other shapes besides a cone may be used for the redirection of light and other arrangements of the diodes may be used.

While some of the embodiments of the present invention have been described in the military context, it should be understood that all of the embodiments are applicable to many circumstances or settings other than military settings.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A hearing protection device comprising:
 a body portion having a channel extending from a first end to a second end, the first end configured to be inserted into an ear canal of a user and positioned proximate a bony interface near an interior end of the ear canal of the ear;

an acoustically limp material placed in direct contact with the first end of the body portion, the acoustically limp material configured to form a hole therein aligned with the channel extending through at least a portion of the body portion; and a film material placed in constant direct contact over an end of the acoustically limp material at the first end of the body portion to cover an outer opening of the hole at the first end, wherein the film material acts as a clamped plate when subject to pressure, wherein the film material acting as the clamped plate when subject to the pressure is configured to be held in the first end of the body portion proximate the bony interface, wherein the film material is further configured to withstand the pressure, including a blast induced shockwave overpressure of at least 1 atmosphere, wherein the blast induced shockwave overpressure is an increased pressure over atmospheric pressure which is associated with a blast and is formed by compression of air in front of a blast wave which heats and accelerates air molecules.

2. The hearing protection device of claim 1 wherein the film material has a thickness of less than or equal to 10 μm.

3. The hearing protection device of claim 1 wherein the film material has a thickness of less than or equal to 6 μm.

4. The hearing protection device of claim 1 wherein the film material has a thickness of less than or equal to 2 μm.

5. The hearing protection device of claim 1 wherein the film material includes a polymer film material.

6. The hearing protection device of claim 5 wherein the polymer film material has a thickness of less than or equal to 10 μm.

7. The hearing protection device of claim 5 wherein the polymer film material has a thickness of less than or equal to 6 μm.

8. The hearing protection device of claim 5 wherein the polymer film material has a thickness of less than or equal to 2 μm.

9. The hearing protection device of claim 1 wherein the hole has a diameter of less than or equal to one millimeter.

10. A hearing protection device comprising:

a body portion having a channel extending from a first end to a second end, the first end configured to be inserted into an ear canal of a user and positioned proximate a bony interface near an interior end of the ear canal of the ear;

an acoustically limp material placed in direct contact with the first end of the body portion, the acoustically limp material configured to form a hole therein aligned with the channel-extending through at least a portion of the body portion; and a film material having a thickness less than 10 μm placed in direct contact over an end of the acoustically limp material at the first end of the body portion about a periphery of the hole to cover an outer opening of the hole at the first end, wherein the film material acts as a clamped plate when subject to pressure, wherein the film material acting as the clamped plate when subject to the pressure is configured to be held in the first end of the body portion proximate the bony interface, wherein the film material is further configured to withstand the pressure, including a blast induced shockwave overpressure of at least 1 atmosphere, wherein the blast induced shockwave overpressure is an increased pressure over atmospheric pressure which is associated with a blast and is formed by compression of air in front of a blast wave which heats and accelerates air molecules.

11. The hearing protection device of claim 10 wherein the film material includes a polymer film material.

12. The hearing protection device of claim 10 wherein the hole has a diameter of less than or equal to one millimeter.

13. A hearing protection device comprising:

a body portion having a channel extending from a first end to a second end, the first end configured to be inserted into an ear canal of a user and positioned proximate a bony interface near an interior end of the ear canal of the ear;

an acoustically limp material placed in direct contact with the first end of the body portion, the acoustically limp material configured to form a hole therein aligned with the channel extending through at least a portion of the body portion, wherein the hole has a diameter of less than or equal to one millimeter; and a film material having a thickness less than 10 μm placed in direct contact over an end of the acoustically limp material at the first end of the body portion about a periphery of the hole to cover an outer opening of the hole at the first end, wherein the film material acts as a clamped plate when subject to pressure, wherein the film material acting as the clamped plate when subject to the pressure is configured to be held in the first end of the body portion proximate the bony interface, wherein the film material is further configured to withstand the pressure, including a blast induced shockwave overpressure of at least 1 atmosphere, wherein the blast induced shockwave overpressure is an increased pressure over atmospheric pressure which is associated with a blast and is formed by compression of air in front of a blast wave which heats and accelerates air molecules.

14. The hearing protection device of claim 13 wherein the film material includes a polymer film material.

15. The hearing protection device of claim 1 wherein the film material has a tensile strength that satisfies $$\sigma m > R/2\tau \sin \alpha \Delta p$$

where,
  σm is tensile strength,
  R is radius,
  τ is thickness,
  α is the angle of deflection, and
  p is pressure.

16. The hearing protection device of claim 1 wherein the acoustically limp material surrounds a circumference of the front end of the body portion.

* * * * *